United States Patent
Müllner et al.

[11] Patent Number: 6,011,051
[45] Date of Patent: Jan. 4, 2000

[54] USE OF ISOXAZOLE AND CROTONAMIDE DERIVATIVES FOR THE MODULATION OF APOPTOSIS

[75] Inventors: Stefan Müllner, Hochheim; Claudia Dax, Gernsheim, both of Germany

[73] Assignee: Hoechst Aktiengesellschaft, Frankfurt am Main, Germany

[21] Appl. No.: 08/898,756

[22] Filed: Jul. 23, 1997

[30] Foreign Application Priority Data

Jul. 31, 1996 [DE] Germany .......................... 196 30 838
Oct. 1, 1996 [DE] Germany .......................... 196 40 555

[51] Int. Cl.[7] .......................... A61K 31/42; A61K 31/36; A61K 31/275
[52] U.S. Cl. .......................... 514/378; 514/521; 514/466; 514/931
[58] Field of Search .................................. 514/378, 521, 514/466, 931

[56] References Cited

U.S. PATENT DOCUMENTS

| | | | |
|---|---|---|---|
| 4,061,767 | 12/1977 | Ertel et al. | 424/282 |
| 4,965,276 | 10/1990 | Bartlett et al. | 514/378 |
| 5,240,960 | 8/1993 | Hambleton et al. | 514/521 |
| 5,268,382 | 12/1993 | Bartlett et al. | 514/378 |
| 5,308,865 | 5/1994 | Bartlett et al. | 514/465 |
| 5,416,112 | 5/1995 | Kuo | 514/521 |
| 5,459,163 | 10/1995 | Bartlett et al. | 514/521 |
| 5,494,911 | 2/1996 | Bartlett et al. | 514/256 |
| 5,504,084 | 4/1996 | Bartlett et al. | 514/236.8 |
| 5,519,042 | 5/1996 | Morris et al. | 514/378 |
| 5,547,970 | 8/1996 | Weithmann et al. | 514/378 |
| 5,547,971 | 8/1996 | Weithmann et al. | 514/378 |
| 5,554,637 | 9/1996 | Weithmann et al. | 514/378 |
| 5,556,870 | 9/1996 | Weithmann et al. | 514/378 |
| 5,624,946 | 4/1997 | Williams | 514/378 |
| 5,856,330 | 1/1999 | Müllner et al. | 514/263 |

FOREIGN PATENT DOCUMENTS

| | | |
|---|---|---|
| 2076555 | 2/1993 | Canada . |
| 2081173 | 4/1993 | Canada . |
| 0 413 329 A2 | 2/1991 | European Pat. Off. . |
| 0 484 223 A2 | 6/1992 | European Pat. Off. . |
| 0529 500 A1 | 3/1993 | European Pat. Off. . |
| 0 538 783 A1 | 4/1993 | European Pat. Off. . |
| 0 551 230 A1 | 7/1993 | European Pat. Off. . |
| 0 665 013 A1 | 8/1995 | European Pat. Off. . |
| WO 95/19169 | 7/1995 | WIPO . |

OTHER PUBLICATIONS

Samstag, Y. et al, *J. of Immunology*, "Inhibition of Constitutive Serine Phosphatase Activity in T Lymphoma Cells Results in Phosphorylation of pp19/Cofilin and Induces Apoptosis", pp. 4167–4173 (1996).

*Primary Examiner*—Theodore J. Criares
*Attorney, Agent, or Firm*—Finnegan, Henderson, Farabow, Garrett & Dunner, L.L.P.

[57] ABSTRACT

Compounds of the formula I or II

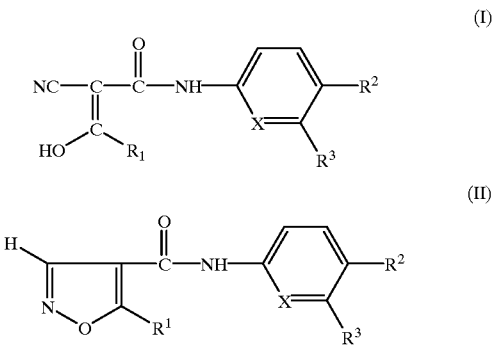

are suitable for the production of pharmaceuticals for the modulation of apoptosis. These compounds can be employed for the treatment of infarct, stroke, neurodegeneration or hypertrophic disorders.

15 Claims, No Drawings

USE OF ISOXAZOLE AND CROTONAMIDE DERIVATIVES FOR THE MODULATION OF APOPTOSIS

In contrast to necrosis, apoptosis is a genetically controlled (programmed) cell death, which is an essential constituent of the life of multicellular organisms.

In contrast to this apoptosis process which is normal and necessary to life, numerous forms of illness or their symptoms are an expression of an abnormal, i.e. a) uncontrolled or b) suppressed apoptosis [a]: infarct, stroke or neurodegeneration, b) hypertrophic disorders]. Healing processes of illnesses can thus be possible by means of suppression or activation of apoptosis (e.g. transverse lesion of the spinal cord, immune defense etc.). Apoptosis proceeds after induction of defined death signals, for example by stimulation of certain receptors (e.g. Fas receptor), via a secondarily induced complex cascade of intermeshing biochemical events, at the end of which is the disintegration of the intact cell to give membrane-packed units, which can be disposed of by the body without or only with slight damage to the surrounding cells (opposite to necrosis). In some cases here the transitions between necrosis and apoptosis are fluid; thus there are cases in which necrosis leads to apoptosis (or conversely) (e.g. infarct, stroke etc.).

As a costimulatory factor in T cells, cofilin, a 19 kDa actin-binding protein, plays a crucial part in the immune reaction. Cofilin is present in the cytosol in phosphorylated form and is transported into the cell nucleus after dephosphorylation. It obviously serves here as a transport molecule for the protein actin, which has no nuclear recognition sequence and is known as a DNAse I inhibitor. By means of this mechanism, the degree of phosphorylation of the cytosolic cofilin can bring a regulating and modulating influence to bear on the apoptosis of cells [J. of Immunology, 156, 4167–4173 (1996)].

It has now been found that compounds I and II are suitable for inhibiting the dephosphorylation of cofilin and thus they have a modulating influence on apoptosis.

The invention therefore relates to the use of at least one compound of the formula I or II

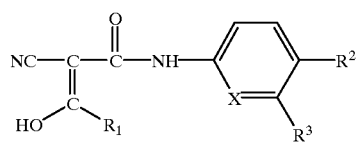

(I)

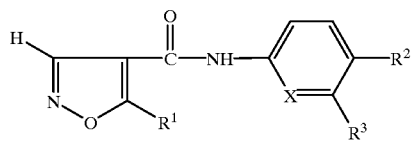

(II)

and/or an optionally stereoisomeric form of the compound of the formula I or II and/or a physiologically tolerable salt of the compound of the formula I or II, where $R^1$ is
a) $(C_1-C_4)$-alkyl
b) $(C_3-C_5)$-cycloalkyl,
c) $(C_2-C_6)$-alkenyl or
d) $(C_2-C_6)$-alkynyl, $R^2$ is
a) —$CF_3$,
b) —O—$CF_3$,
c) —S—$CF_3$,
d) —OH,
e) —$NO_2$,
f) halogen,
g) benzyl,
h) phenyl,
i) —O-phenyl,
k) —CN or
l) —O-phenyl, mono- or polysubstituted by
  1) $(C_1-C_4)$-alkyl,
  2) halogen,
  3) —O—$CF_3$ or
  4) —O—$CH_3$, $R^3$ is
a) (Chd 1–$C_4$)-alkyl,
b) halogen, or
c) a hydrogen atom, and X is
a) a —CH group or
b) a nitrogen atom, for the production of pharmceuticals for the modulation of apoptosis.

The use is preferred of a compound of the formula I or II and/or an optionally stereoisomeric form of the compound of the formula I or II and/or a salt of the compound of the formula I or II, where $R^1$ is
a) methyl,
b) cyclopropyl or
c) $(C_3-C_5)$-alkynyl, $R^2$ is —$CF_3$ or —CN, $R^3$ is a hydrogen atom or methyl, and X is a —CH group.

The use is in particular preferred of N-(4-trifluoromethylphenyl)-2-cyano-3-hydroxycrotonamide, 2-cyano-3-cyclopropyl-3-hydroxyacrylic acid (4-cyanophenyl)amide or N-(4-trifluoromethylphenyl)-2-cyano-3-hydroxyhept-2-en-6-ynecarboxamide.

The preparation of the compounds of the formulae I and II is carried out according to known processes, such as are described in EP 484 223, EP 529 500, U.S. Pat. No. 4,061,767, EP 538 783, or EP 551 230, the disclosure of which is hereby incorporated by reference.

The term "alkyl," "alkenyl" or "alkynyl" is understood as meaning radicals whose carbon chain can be straight-chain or branched. Furthermore, the alkenyl or alkynyl radicals can also contain one or more double bonds or one or more triple bonds. Cyclic alkyl radicals are, for example, 3- to 5-membered monocycles such as cyclopropyl, cyclobutyl or cyclopentyl.

As used herein, the term "modulation of apoptosis" is understood as meaning the inhibition or induction of apoptosis.

As used herein, the term "therapeutically effective amount" means an amount of the compound which is effective in treating the named disorder. A therapeutically effective amount can be readily determined by the attending diagnostician, as one skilled in the art, by the use of known techniques and by observing results obtained under analogous circumstances.

As used herein, the term "patient" refers to a mammal such as a dog, cat, guinea pig, mouse, rat or human being.

The terms "treating" or "to treat" means to alleviate symptoms, eliminate the causation either on a temporary or permanent basis, or to prevent or slow the appearance of symptoms of the named disorder.

The starting substances of the chemical reactions are known or can be easily prepared by methods known from the literature.

The present invention provides a pharmaceutical composition effective for use as a pharmaceutical in the treatment of a disorder with uncontrolled apoptosis comprising at least one compound of the formula I and/or II and/or optionally stereoisomeric form of the compound of the formula I or II and/or a physiologically tolerable salt of the compound of the formula I or II as active substance. The pharmaceutical composition can be administered according to the present invention in any suitable form or mode which makes the compound bioavailable in effective amounts. The pharmaceutical composition may be administered with a physiologically acceptable excipient and further suitable active compounds, additives or auxiliaries.

The pharmaceuticals according to the invention are administered parenterally, orally or rectally or, if appropriate, also applied topically.

Suitable solid or liquid pharmaceutical preparation forms are, for example, granules, powders, coated tablets, tablets, (micro)capsules, suppositories, syrups, juices, suspensions, emulsions, drops or injectable solutions and also preparations with sustained release of active compound, in whose preparation customary auxiliaries, such as excipients, disintegrants, binders, coating agents, swelling agents, glidants or lubricants, flavorings, sweeteners or solubilizers, are used. Frequently used auxiliaries which may be mentioned are, for example, titanium dioxide, magnesium carbonate, lactose, mannitol and other sugars, talc, lactoprotein, gelatin, starch, cellulose and its derivatives, animal and vegetable oils, polyethylene glycols and solvents, such as, for example, sterile water and mono- or polyhydric alcohols, e.g. glycerol.

Due to the pharmacological properties of the compound of the formula I or II, these compounds can be employed for the specific modulation of apoptosis. Therefore, the present invention also provides a method of treating a disorder with uncontrolled apoptosis in a patient comprising administering a therapeutically effective amount of a compound of the formula I and/or II and/or optionally stereoisomeric form of the compound of the formula I or II and/or a physiologically tolerable salt of the compound of the formula I or II.

Disorders with uncontrolled apoptosis are, for example, infarct, stroke, transplants, autoimmune disorders, inflammations, neurodegeneration, myoma, muscular atrophy, muscular dystrophy, cachexia, systemic inflammation response syndrome (SIRS), adult respiratory distress syndrome (ARDS), cerebral malaria, pulmonary sarcosidosis, enteritis, chronic pneumonia, reperfusion damage, scar formation, burn damage, acquired immune deficiency syndrome (AIDS), cancer, disorders with increased protein loss, chronic renal insufficiency or hypertrophic disorders.

The identification of those patients who would benefit from the present invention is well within the ability and knowledge of one skilled in the art. A clinician skilled in the art can readily identify, by the use of clinical tests, physical examination and medical/family history, those patients who are suffering from a disorder with uncontrolled apoptosis.

Preferably, the preparation is prepared and administered in dose units, each unit containing as active constituent a certain dose of the compound of the formula I and/or II and/or physiologically tolerable salts of the compound of the formula I or II. For the treatment of a patient (70 kg), in early phases an intravenous infusion treatment of at most 350 mg per day is indicated. In the later rehabilitation phase two to three doses in an amount from 2 mg to 250 mg, preferably 5 mg to 150 mg, in particular 10 mg to 50 mg, particularly preferably 10 mg to 20 mg, of the compound of the formula I and/or II and/or the corresponding salts of the compound of the formula I are indicated. The dose to be used is of course dependent on various factors such as the living being to be treated (i.e. human or animal), age, weight, general state of health, the degree of severity of the symptoms, the disorder to be treated, possible concomitant disorders (if present), the nature of the concomitant treatment with other pharmaceuticals, or frequency of the treatment. The doses are in general administered several times per day and preferably once to three times per day. The amounts of compound of the formula I used are based in this case on the recommended daily dose of the respective compound of the formula I or II and the solubility of the compound I or II.

Furthermore, the compounds of the formula I or II and/or, if appropriate, their corresponding salts, can also be administered together with a therapeutically effective amount of other suitable active compounds, for example antiuricopathics, analgesics, steroidal or nonsteroidal antiinflammatories, platelet aggregation inhibitors or immunosuppressant compounds such as cyclosporin A, FK 506 or rapamycin.

The disclosures of German application serial nos. 19630838.0 filed Jul. 31, 1996 and 19640555.6 filed Oct. 1, 1996 are herein incorporated by reference.

EXAMPLE 1

Pharmacological Testing 1.1 Cell Culture

The murine macrophage cell line RAW 264.7 was obtained from ATCC (Rockville, Md.) and cultured in DMEM (Sigma, St. Louis, Mo.) with 4.5 g of glucose/l, 110 mg of sodium pyruvate/l, 10% of heat-inactivated FCS (Gibco, Grand Island, N.Y.) and penicillin/streptomycin (50 U/50 mg/ml).

The macrophages were passaged every 2–3 days and one day before the start of the experiment applied at $2.10^6$ cells to tissue culture flasks (75 $cm^2$, Falcon, Becton Dickinson GmbH, Heidelberg, Germany). The cells were supplied with fresh medium and the preparations were added in the appropriate concentrations. N-(4-Trifluoromethylphenyl-2-cyano-3-hydroxycrotonamide sodium salt (compound 1) was dissolved in cell medium at 20 mM. Of this, 100 ml each (60 mM final concentration), 33 ml (20 mM final concentration) and 16.7 ml (10 mM final concentration) were pipetted into 20 ml of medium. Stimulation with lipopolysaccharide (LPS; *E. coli*, serotype 0127: B 8; Sigma, St. Louis, Mo.) at a concentration of 10 ng/ml was carried out 1 hour after preincubation with the preparation.

Aliquots of a stock solution of lipopolysaccharides (LPS 1 mg/ml in 10% dimethyl sulfoxide (DMSO)) were diluted with medium to a concentration of 1 mg/ml and stored at −20° C. The cells were incubated in 10% $CO_2$ for 24 hours (h) at 37° C.

1.2 Sample preparation

All chemicals used were analytically pure or of electrophoresis quality and were obtained from Millipore Co. (Bedford, Mass.) or Sigma (St. Louis, Mo.), if other sources of supply are not indicated separately.

The 2-D electrophoresis (2-DE) was carried out using the Investigator System® (Millipore), and the samples were worked up according to the procedure of the manufacturer with small changes. The adherent murine macrophages, standing on ice, were washed three times every 60 seconds with 10 ml of ice-cold PBS. The cells were then lyzed in 1 ml of boiling lysis buffer, consisting of 0.3 g of SDS, 3.088 g of DTT, 0.444 g of tris HCl and 0.266 g of tris base in 100 ml. The cell lyzate was scraped off and heated in boiling water in a 2 ml sample vessel for 10 minutes (min). Polynucleotides were cleaved at 37° C. in 30 min by addition of Benzonase® (Merck, Darmstadt, Germany). At this point in the sample preparation, an aliquot was taken, and the protein content was determined by the method of Popov.

For the 2-DE the proteins of the sample were precipitated by dropwise addition to ice-cold acetone (80% v/v). The sample was cooled on ice for 20 min and then centrifuged at 240 g for 10 min. The dried pellet was taken up in one part of lysis buffer and four parts of a sample buffer to give a protein content of 5 mg/ml. The sample buffer consists of 59.7 g of urea, 4.0 ml of NP-40, 1.54 g of DTT, 5.5 ml of carrier ampholytes (pH 3–10, 2-DE optimized) in 100 ml. Undissolved material was separated off before electrophoresis by centrifugation of the samples at 16000×g.

1.3 2-DE Gel Electrophoresis

High-resolution two-dimensional gel electrophoresis was carried out according to the method of O'Farrell with modifications, such as were described by Garrels. To do this, the Millipore Investigator® 2-D electrophoresis system (Millipore Co., Bedford, Mass.) was employed.

Isoelectric focussing was carried out in glass capillaries (1 mm in diameter) using a 0.08 mm thick fiber which prevents expansion and breaking of the rod. The IEF gel consists of a 4.1% T, 2.4% C polyacrylamide matrix which was prepared from a 30.8% T, 2.6% C stock solution, 9.5 M urea, 2.0% (v/v) NP-40, 10 mM CHAPS and 2% (v/v) carrier ampholytes (pH 3–10, 2-DE optimized).

0.01 M $H_3PO_4$, was used as anode buffer, 0.1 M NaOH as cathode buffer. Before the prefocussing to form the pH gradient, 15 ml of a sample coating buffer, consisting of 0.5 M urea, 0.2% (v/v) NP-40, 0.1% (v/v) carrier ampholytes and 50 mM DTT, were applied. The voltage maximum of 1500 volts was reached within 90 minutes at a maximum current of 110 mA/gel. After prefocussing, 20 ml of the sample (100 mg of protein) and a further 15 ml of coating buffer were applied.

Isoelectric focussing of the proteins took place within 18000 Vh. After completion of the electrophoresis, the rods were cooled on ice and equilibrated in a buffer consisting of 0.3 M tris base, 0.075 M tris HCl, 6% SDS, 50 mM DTT and 0.01% Bromophenol Blue. The rod gels were transferred directly to the surface of the vertical gel of the second dimension or stored at −20° C. until use. The second dimension was carried out in an SDS gradient gel (10–17%) without collecting gel.

The gradient was produced by mixing two gel solutions. A: 100 ml of acrylamide (30.5% T, 1.64% C), 73 ml of tris (1.5 M, pH 8.8), 123 ml of $H_2O$, 3 ml of SDS (10%), 150 ml of TEMED and 750 ml of ammonium peroxodisulfate (10%).
B: 170 ml of acrylamide, 73 ml of tris, 66.78 g of glycerol, 3 ml of SDS, 150 ml of TEMED, 750 ml of ammonium peroxodisulfate.

Electrophoresis was carried out overnight at constant temperature in a running buffer consisting of 25 mM tris base, 192 mM glycine and 0.1% SDS until the Bromophenol Blue front was approximately 1 cm distant from the end of the gel. After completion of the electrophoresis, the proteins in the gel were stained with silver reagent according to Heukeshoven and Dernick.

The analysis of the 2-D gels and the preparation of synthetic images were carried out using the BioImage System (BioImage Systems Co.). The protein pattern obtained was scanned by a Kodak Megaplus camera model 1.4 and the data were processed by a HAM station.

1.4 Results

The results of the unstimulated control were set equal to 100%. The addition of LPS (10 ng/ml) led to a 50% dephosphorylation of cofilin. The simultaneous application of LPS (10 ng/ml) and compound 1 (60 mM), however, led to no dephosphorylation of cofilin. Therefore, in the presence of compound 1, a 100% inhibition of the dephosphorylation of cofilin in the macrophages results, in comparison with the inhibition which was achieved in the case of the macrophages only treated with LPS.

The addition of LPS (10 ng/ml) and 20 mM compound 1 or 10 mM compound 1 resulted in the same dephosphorylation of cofilin as without addition of compound 1. Therefore 20 mM or 10 mM of the compound 1 no longer lead to an inhibition of the dephosphorylation of cofilin.

What is claimed is:

1. A method of treating a disorder with uncontrolled apoptosis in a patient comprising administering a therapeutically effective amount of a compound of the formula I and/or II

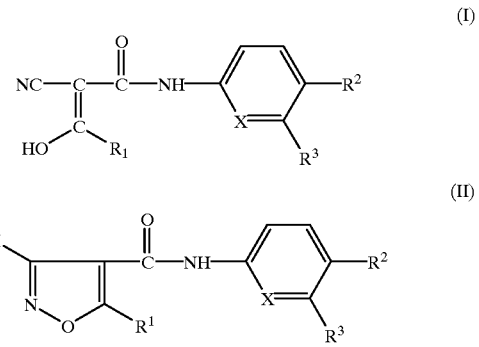

and/or optionally stereoisomeric form of the compound of the formula I or II and/or a physiologically tolerable salt of the compound of the formula I or II, where $R^1$ is
   a) $(C_1-C_4)$-alkyl
   b) $(C_3-C_5)$-cycloalkyl,
   c) $(C_2-C_6)$-alkenyl or
   d) $(C_2-C_6)$-alkynyl, $R^2$ is
   a) —$CF_3$,
   b) —O—$CF_3$,
   c) —S—$CF_3$,
   d) —OH,
   e) —$NO_2$,
   f) halogen,
   g) benzyl,
   h) phenyl,
   i) —O-phenyl,
   k) —CN or
   l) —O-phenyl, mono- or polysubstituted by
     1) $(C_1-C_4)$-alkyl,
     2) halogen,
     3) —O—$CF_3$ or
     4) —O—$CH_3$, $R^3$ is
   a) $(C_1-C_4)$-alkyl,
   b) halogen, or
   c) a hydrogen atom, and X is
- a) a —CH group or
- b) a nitrogen atom.

2. A method according to claim 1 wherein $R^1$ is
- a) methyl,
- b) cyclopropyl or
- c) $(C_3–C_5)$-alkynyl, $R^2$ is $CF_3$ or CN, $R^3$ is a hydrogen atom or methyl, and X is a —CH— group.

3. A method according to claim 2 wherein the compound is N-(4-trifluoromethyl-phenyl)-2-cyano-3-hydroxycrotonamide.

4. A method according to claim 2 wherein the compound is 2-cyano-3-cyclopropyl-3-hydroxyacrylic acid (4-cyanophenyl)amide.

5. A method according to claim 2 wherein the compound is N-(4-trifluoro-methylphenyl)-2-cyano-3-hydroxyhept-2-en-6-yne-carboxamide.

6. A method according to claim 1 wherein the disorder with uncontrolled apoptosis is from the group of infarct, stroke, transplants, autoimmune disorders, inflammations, neurodegeneration, myoma, muscular atrophy, cachexia, muscular dystrophy, systemic inflammation response syndrome (SIRS), adult respiratory distress syndrome (ARDS), cerebral malaria, scar formation, pulmonary sarcosidosis, enteritis, chronic pneumonia, reperfusion damage, burn damage, acquired immune deficiency syndrome (AIDS), cancer, disorders with increased protein loss, chronic renal insufficiency or hypertrophic disorders.

7. A method according to claim 6 wherein the disorder with uncontrolled apoptosis is infarct.

8. A method according to claim 6 wherein the disorder with uncontrolled apoptosis is stroke.

9. A method according to claim 6 wherein the disorder with uncontrolled apoptosis is inflammation.

10. A method for inhibiting the dephosphorylation of the protein cofilin comprising administering to a patient in need thereof a compound of the formula I and/or II as defined in claim 1.

11. A method according to claim 1 comprising administering to said patient an amount of said compound from about 2 mg to 250 mg.

12. A method according to claim 11 wherein said amount is from about 10 mg to 50 mg.

13. A method according to claim 1 additionally comprising administering a therapeutically effective amount of at least one active substance from the group of antiuricopathics, analgesics, steroidal or nonsteroidal antiinflammatories, platelet aggregation inhibitors or immunosuppressant compounds.

14. A method according to claim 13 wherein said active substance is cyclosporin A, FK 506 or rapamycin.

15. A pharmaceutical composition comprising an amount of at least one compound of formula I and/or formula II as defined in claim 1 effective for use as a pharmaceutical in the treatment of a disorder with uncontrolled apoptosis.

* * * * *